US011896819B2

(12) United States Patent
Rosa et al.

(10) Patent No.: US 11,896,819 B2
(45) Date of Patent: Feb. 13, 2024

(54) SPINAL CORD STIMULATION SYSTEMS, METHODS, AND DEVICES

(71) Applicant: NeuroOne Medical Technologies Corporation, Eden Prairie, MN (US)

(72) Inventors: Dave Rosa, Eden Prairie, MN (US); Thomas Bachinski, Lakeville, MN (US); Doug Weber, Eden Prairie, MN (US); Vanessa Tolosa, Emeryville, CA (US); Derek Johnson, Chanhassen, MN (US)

(73) Assignee: NeuroOne Medical Technologies Corporation, Eden Prairie, MN (US)

( * ) Notice: Subject to any disclaimer, the term of this patent is extended or adjusted under 35 U.S.C. 154(b) by 0 days.

(21) Appl. No.: 16/992,023

(22) Filed: Aug. 12, 2020

(65) Prior Publication Data

US 2021/0046305 A1 Feb. 18, 2021

Related U.S. Application Data

(60) Provisional application No. 62/885,555, filed on Aug. 12, 2019.

(51) Int. Cl.
*A61N 1/05* (2006.01)

(52) U.S. Cl.
CPC ......... *A61N 1/0553* (2013.01); *A61N 1/0558* (2013.01)

(58) Field of Classification Search
CPC ... A61N 1/0553; A61N 1/0558; A61N 1/0448
USPC .......................................................... 607/117
See application file for complete search history.

(56) References Cited

U.S. PATENT DOCUMENTS

| | | | |
|---|---|---|---|
| 7,337,012 B2 | 2/2008 | Maghribi et al. | |
| 8,798,769 B1 | 8/2014 | Parker, Jr. | |
| 9,020,608 B2 * | 4/2015 | Swanson | A61N 1/0553 607/117 |
| 9,314,618 B2 * | 4/2016 | Imran | H05K 1/118 |
| 10,118,030 B2 | 11/2018 | Pellinen et al. | |
| 2007/0088417 A1 * | 4/2007 | Schouenborg | A61B 5/4076 607/116 |
| 2008/0039917 A1 | 2/2008 | Cross et al. | |
| 2012/0143296 A1 | 6/2012 | Pianca et al. | |
| 2013/0005169 A1 * | 1/2013 | Soltis | A61N 1/0558 439/278 |
| 2013/0312258 A1 * | 11/2013 | Swanson | H01R 24/58 29/854 |
| 2015/0066122 A1 * | 3/2015 | Govea | A61N 1/05 607/116 |
| 2017/0340891 A1 * | 11/2017 | Boggs | A61B 17/3403 |
| 2018/0008821 A1 | 1/2018 | Gonzalez et al. | |
| 2018/0117313 A1 * | 5/2018 | Schmidt | A61N 1/3752 |
| 2018/0126156 A1 * | 5/2018 | Sparks | A61B 6/12 |

* cited by examiner

*Primary Examiner* — Carl H Layno
*Assistant Examiner* — Jane C Kalinock
(74) *Attorney, Agent, or Firm* — Fredrikson & Byron, P.A.

(57) ABSTRACT

Disclosed herein are various spinal cord stimulation devices with thin film components, including a device having a flexible section disposed along a length of the elongate lead body of the device. Other stimulation devices have a flexible section disposed within the electrode body of the device. Further devices include both a flexible section disposed within the elongate lead body and a flexible section disposed within the electrode body of the device.

17 Claims, 11 Drawing Sheets

52 54 50 52 54 50

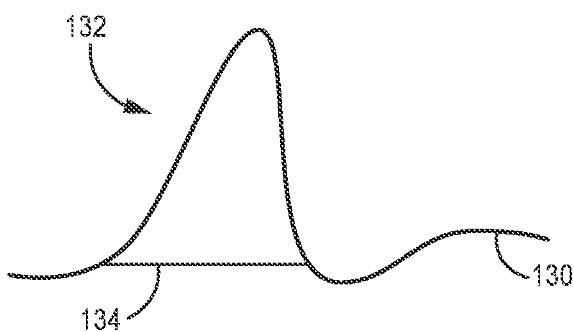
FIG. 11A
FIG. 11B
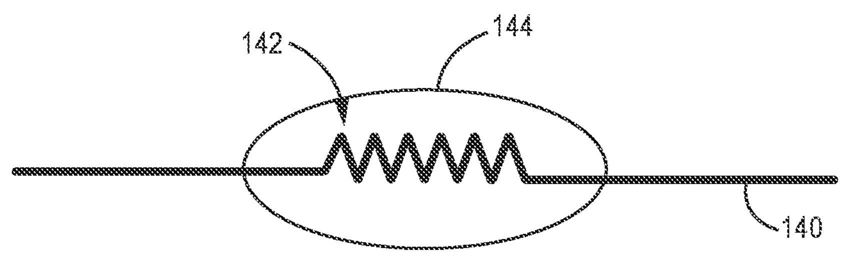
FIG. 12A
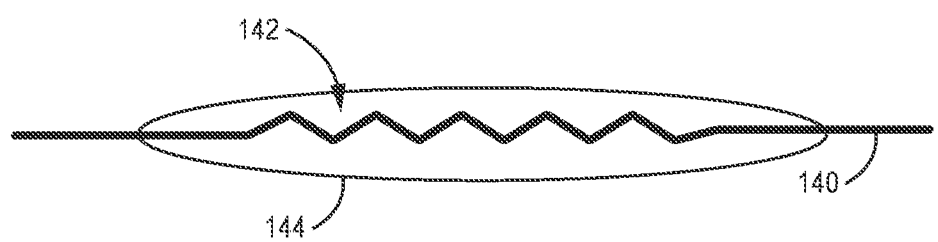
FIG. 12B
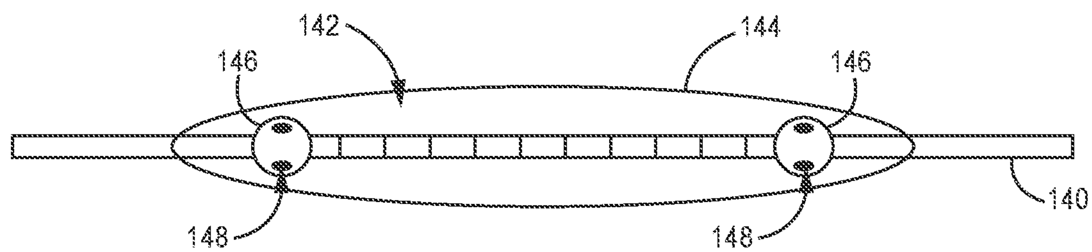
FIG. 12C

SPINAL CORD STIMULATION SYSTEMS, METHODS, AND DEVICES

CROSS-REFERENCE TO RELATED APPLICATION(S)

This application claims the benefit under 35 U.S.C. § 119(e) to U.S. Provisional Application 62/885,555, filed Aug. 12, 2019 and entitled "Spinal Cord Stimulation Systems, Methods, and Devices," which is hereby incorporated herein by reference in its entirety.

FIELD

The various embodiments herein relate to stimulation devices for stimulating the spinal cord and/or peripheral nerves and related systems and methods.

BACKGROUND

Electrical stimulation of the spinal cord or peripheral nerves can result in pain reduction and/or elimination. Medical devices having electrodes (also referred to as "stimulators" or "leads") are often implanted near the spinal column to provide pain relief for chronic intractable pain. The electrodes stimulate tissue within the spinal column to reduce pain sensations at other parts of the body. The stimulation signals applied can be optimized for pain reduction or elimination depending on the location of the pain.

Known stimulation devices are typically percutaneous or paddle leads. One disadvantage of each type of lead is that the device often is often displaced after implantation, typically as a result of the movement of the patient. That is, after implantation, scar tissue forms around and attaches to the lead. Subsequently, movement by the patient causes natural movement of the spine, which can cause the scar tissue to pull away from the lead, thereby displacing the lead.

Other limitations of the known leads will also become evident in the Detailed Description.

There is a need in the art for improved spinal cord stimulation devices and related systems and methods.

BRIEF SUMMARY

Discussed herein are various spinal cord stimulation devices and methods of implanting the same into a patient.

In Example 1, a spinal cord stimulation device comprises an elongate lead body, an electrode body disposed at one end of the elongate lead body, and a flexible section disposed along a length of the elongate lead body, wherein the elongate lead body is a thin film component.

Example 2 relates to the spinal cord stimulation device according to Example 1, further comprising at least two attachment barbs disposed on the electrode body.

Example 3 relates to the spinal cord stimulation device according to Example 1, wherein the flexible section has a first end coupled to a distal portion of the elongate lead body and a second coupled to a proximal portion of the elongate lead body.

Example 4 relates to the spinal cord stimulation device according to Example 1, wherein the stimulation device is a percutaneous lead device or a paddle lead device.

Example 5 relates to the spinal cord stimulation device according to Example 1, wherein the flexible section is moveable between a retracted configuration and an extended configuration.

Example 6 relates to the spinal cord stimulation device according to Example 1, wherein the flexible section comprises an S-shaped configuration, wherein the S-shaped configuration is moveable between a retracted configuration and an extended configuration.

Example 7 relates to the spinal cord stimulation device according to Example 6, wherein the flexible section comprises a tubular component, wherein the S-shaped configuration is disposed within the tubular component.

Example 8 relates to the spinal cord stimulation device according to Example 7, further comprising at least one flexible restraint, wherein the at least one flexible restraint is attached to the S-shaped configuration.

Example 9 relates to the spinal cord stimulation device according to Example 8, wherein the at least one flexible restraint is attached at a first end to the S-shaped configuration and is attached at a second end to the tubular component.

Example 10 relates to the spinal cord stimulation device according to Example 1, wherein the flexible section comprises an accordion-like configuration, a plurality of folds or curves, a spiral configuration, a mesh configuration, or a plurality of cords.

Example 11 relates to the spinal cord stimulation device according to Example 1, further comprising an elastic membrane disposed around the flexible section.

Example 12 relates to the spinal cord stimulation device according to Example 1, further comprising a flexible section disposed within the electrode body.

In Example 13, a spinal cord stimulation device comprises an elongate lead body, an electrode body disposed at one end of the elongate lead body, and a flexible section disposed within the electrode body, wherein the elongate lead body is a thin film component.

Example 14 relates to the spinal cord stimulation device according to Example 13, further comprising at least two attachment barbs disposed on the electrode body.

Example 15 relates to the spinal cord stimulation device according to Example 13, wherein the stimulation device is a percutaneous lead device or a paddle lead device.

Example 16 relates to the spinal cord stimulation device according to Example 13, wherein the flexible section is moveable between a retracted configuration and an extended configuration.

Example 17 relates to the spinal cord stimulation device according to Example 13, wherein the flexible section comprises a mesh configuration or a plurality of cords.

Example 18 relates to the spinal cord stimulation device according to Example 13, further comprising a flexible section disposed along the length of the elongate lead body.

In Example 19, a spinal cord stimulation device comprises an elongate lead body and a deployable electrode array disposed at one end of the elongate lead body. Further, the deployable electrode array comprises a plurality of electrode contacts disposed on the deployable electrode array, a delivery configuration in which the deployable electrode array has a reduced profile, a deployed configuration in which the deployable electrode array has an expanded, flat profile, and a deployment mechanism associated with the deployable electrode array, wherein the deployment mechanism is configured to urge the deployable electrode array into the deployed configuration. In addition, the elongate lead body and the deployable electrode array are thin film components.

Example 20 relates to the spinal cord stimulation device according to Example 19, wherein the device is positionable within a delivery shaft.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 11A is a side view of a flexible section with a flexible restraint in a retracted configuration, according to one embodiment.

FIG. 11B is a side view of the flexible section of FIG. 11A in an extended configuration, according to one embodiment.

FIG. 12A is a side view of a flexible section having a set of folds or curves in an elastic membrane in a retracted configuration, according to one embodiment.

FIG. 12B is a side view of the flexible section of FIG. 12A in an extended configuration, according to one embodiment.

FIG. 12C is a side view of a flexible section with two tabs in an elastic membrane, according to an alternative embodiment.

DETAILED DESCRIPTION

The various embodiments disclosed or contemplated herein relate to improved systems, devices, and methods, and various components thereof, for stimulating the spinal cord or related peripheral nerves in the human body. In certain exemplary implementations, each of the various stimulation systems and devices incorporates thin-film technology and a flexible (and in some cases elastic) section that absorbs or otherwise allows for movement of the patient without resulting in displacement of the device.

Figure 1:
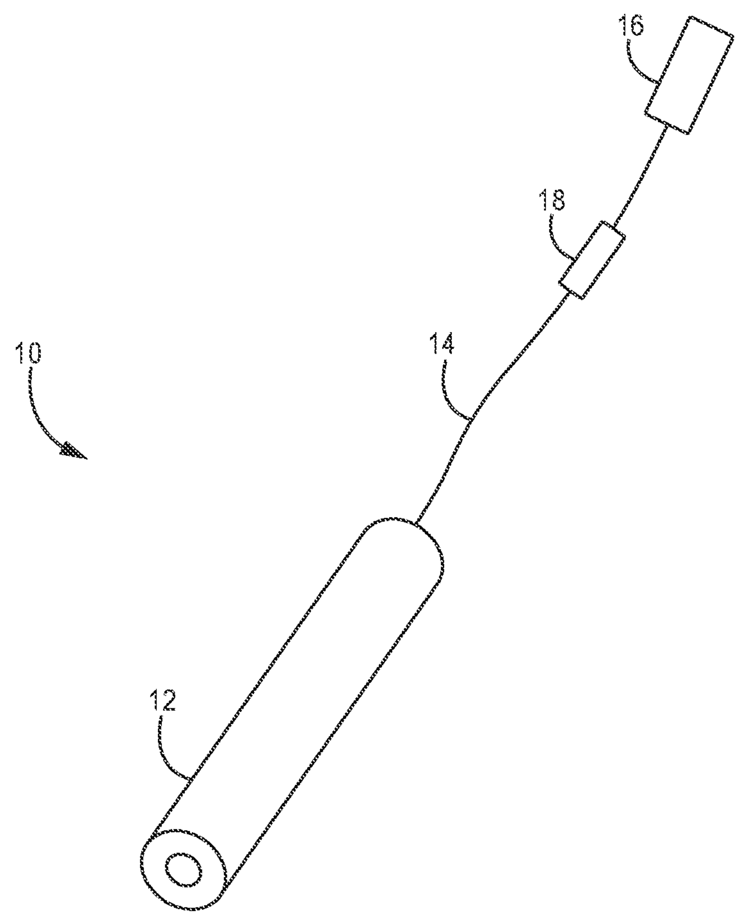
FIG. 1 is a perspective view of a percutaneous lead device, according to one embodiment.
Figure 2:
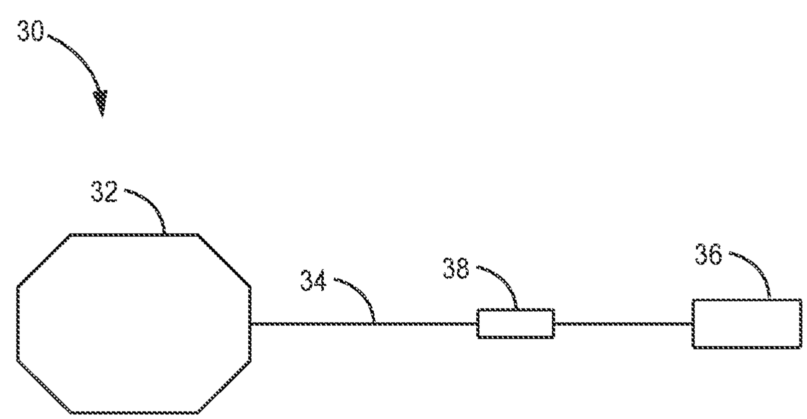
FIG. 2 is a side view of a paddle lead device, according to one embodiment.

FIGS. 1 and 2 each depict a stimulation device 10, 30 for use in stimulation of a patient's spinal cord or peripheral nerves. More specifically, the lead 10 in FIG. 1 is a percutaneous lead 10 having an electrode body 12 on which the one or more electrodes (not shown) are disposed, a lead body (also referred to as a "tail") 14, a connection component (also referred to as a "connector") 16 to which the external electrical source is coupled, and a flexible and/or elastic section 18 along the length of the lead body 14. The lead 30 in FIG. 2 is a paddle lead 30 having an electrode body (also referred to as a "paddle") 32 on which the one or more electrodes (not shown) are disposed, a tail 34, a connector 36, and a flexible and/or elastic section 38 along the length of the tail 34.

It is understood that the corresponding components on each of the above devices 10, 30 are substantially the same and that any discussion of such components with respect to one embodiment can apply to any corresponding component in any implementation disclosed or contemplated herein.

In both of the device embodiments 10, 30 above, the flexible section 18, 38 is any mechanism or feature on or associated with the lead body 14, 34 that can provide for flexibility of that body 14, 34. More specifically, the flexible section 18, 38 provides some flexibility, elasticity, malleability, or extendability to the lead body 14, 34 at the flexible section 18, 38 that allows the device 10, 30 (or any device embodiment disclosed or contemplated herein) to avoid displacement after implantation in the body of a patient. That is, after implantation, when movement of the patient's spine causes movement of the electrode body 12, 32 that places strain or force of any kind on the lead body 14, 34, the flexible section 18, 38 absorbs, releases, or otherwise eliminates that strain or force via the flexibility thereof, thereby minimizing or eliminating the risk of displacement of the device 10, 30.

In various implementations herein, both the electrode body 12, 32 and the lead body 14, 34 are both thin film components. For purposes of this application, the term "thin film" can mean a microscopically thin layer of material that is deposited onto a metal, ceramic, semiconductor or plastic base, or any device having such a component. Alternatively, for purposes of this application, it can also mean a component that is less than about 0.005 inches thick and contains a combination of conductive and dialectric layers. Finally, it is also understood, for purposes of this application, to have the definition that is understood by one of ordinary skill in the art.

The electrode body 12, 32 can, in certain implementations, be made, at least in part, of a polyimide material, such as Kapton® from DuPont®. Alternatively, the body 12, 32 can be made of any other known flexible material for use in spinal stimulation devices such that the body 12, 32 can easily deform to match or otherwise accommodate the shape of the target tissue. In addition, the body 12, 32 in certain embodiments has thin film components. Further, it is understood that the body 12, 32 can be made according to any known process, including any known thin film processing.

The lead body 14, 34 can also be formed from a thin conductive film. For example, in one specific embodiment, the lead body 14, 34 is made of a polyimide film with a conductive film (or separate elongate conductive elements) disposed thereon. Alternatively, the film can be any known thin conductive film.

The various devices herein (including devices 10, 30), according to certain implementations, are configured to be positionable through a needle, including, for example, a 10-gauge needle. Thus, the width of the lead body 14, 34 in some embodiments is less than 0.1 inches. Thus, the various devices allow for percutaneous delivery of an array of electrodes to the epidural space (or other known target area) of a patient via such a needle.

Figure 3A:
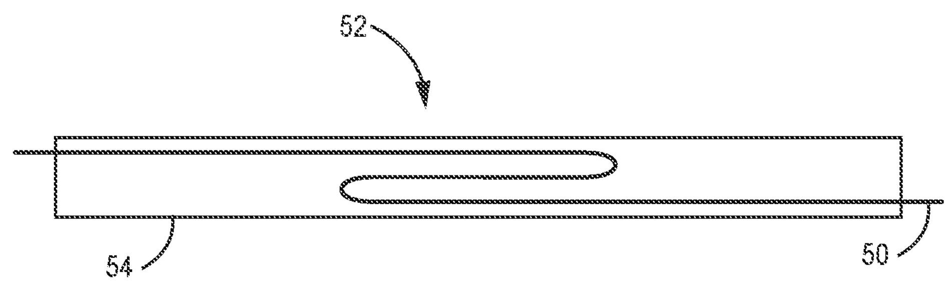
FIG. 3A is a side view of an S-shaped flexible section in a retracted configuration, according to one embodiment.
Figure 3B:
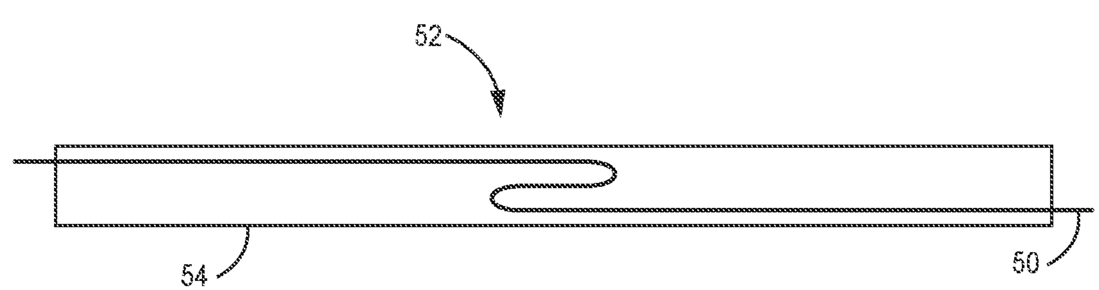
FIG. 3B is a side view of the S-shaped flexible section of FIG. 3A in an extended configuration, according to one embodiment.

One example of a flexible section 52, according to one embodiment, is set forth in FIGS. 3A and 3B. In this implementation, the flexible section 52 is a S- or Z-shaped portion 52 of a lead body 50, which is a thin-film lead body 50. It is understood that the S-shaped section 52 in this embodiment and any other embodiment disclosed or contemplated herein can be a length of the lead body 50 that is overlapping. More specifically, a length of the lead body 50 is folded, bent, or otherwise deformed such that the length is disposed adjacent to another length of the same lead body 50 as shown. Further, the lead body 50 is disposed through a tubular component (also referred to as a "tube") 54 that can also be sized to fit through a needle as described above. As such, in one implementation, the tube 54 is less than 0.1 inches.

The S-shaped section 52, in one embodiment, has two configurations: an unextended or equilibrium configuration as depicted in FIG. 3A and an extended or tensioned configuration as shown in FIG. 3B. When no force is being applied to the lead body 50, the S-shaped section 52 is configured to return to or remain in the unextended configuration as shown in FIG. 3A. However, when any force is applied to either end of the lead body 50 such that one portion is pulled or urged away from another portion thereof, the S-shaped section 52 can extend into its extended configuration as shown in FIG. 3B, thereby reducing the chances of the entire device (not shown) of which the lead body 50 is a part from moving and being displaced as a result of the movement. In this embodiment, the natural or equilibrium state of the unextended configuration is created by a shape memory material that is incorporated into the S-shaped section 52. Alternatively, any feature that can result in the S-shaped section 52 being urged back to its unextended state can be used.

Figure 4A:
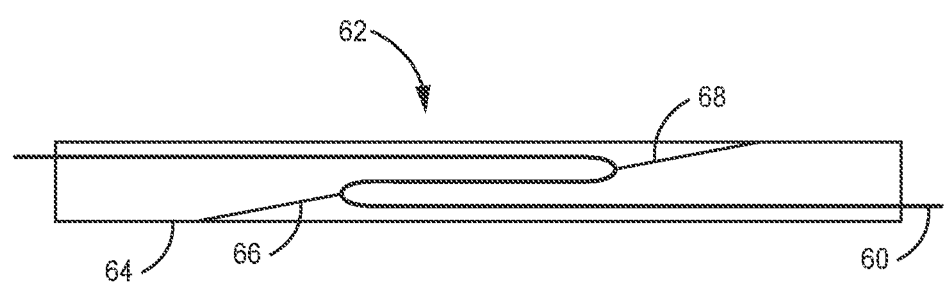
FIG. 4A is a side view of an S-shaped flexible section with flexible restraints in a retracted configuration, according to one embodiment.
Figure 4B:
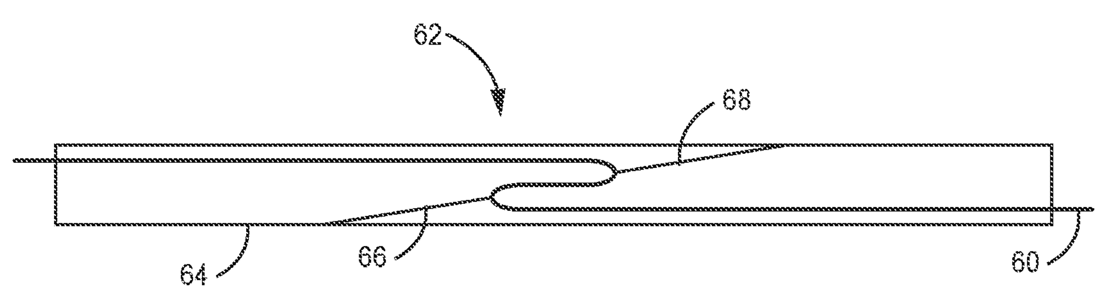
FIG. 4B is a side view of the S-shaped flexible section of FIG. 4A in an extended configuration, according to one embodiment.

Another example of a flexible section 62, according to another embodiment, is set forth in FIGS. 4A and 4B. In this implementation, the flexible section 62 is a S- or Z-shaped portion 62 of a lead body 60, which is a thin-film lead body 60. The lead body 60 is disposed through a tube 64 that can be sized to fit through a needle as described above. As such, in one implementation, the tube 64 is less than 0.1 inches. In addition, the flexible section 62 of the lead body 60 has flexible restraints 66, 68 attached thereto such that the restraints 66, 68 are attached to the flexible section 62 and also to the tube 64 as shown. Thus, in this embodiment, the flexible restraints 66, 68 are the mechanisms by which the flexible section 62 is urged back to its unextended configuration as best shown in FIG. 4A. It is understood that the flexible restraints 66, 68 represent any mechanisms or features that can be coupled to both the S-shaped section 62 and the tube 64 and can be used to urge the S-shaped section 62 back to its unextended configuration.

In use, like the S-shaped section 52 described above, the S-shaped section 62 has an unextended configuration as depicted in FIG. 4A and an extended configuration as shown in FIG. 4B. The description of those configurations and the operation of the S-shaped section 52 above and the benefits thereof apply equally to this S-shaped section 62. Further, in this embodiment, as mentioned above, the S-shaped section 62 is returned to its unextended configuration with the assistance of the flexible restraints 66, 68.

Figure 5A:
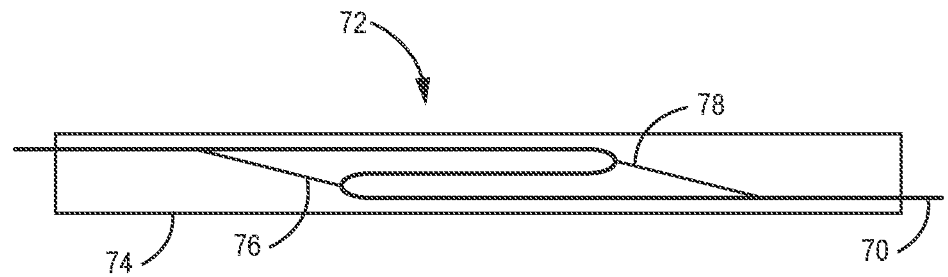
FIG. 5A is a side view of an S-shaped flexible section with flexible restraints in a retracted configuration, according to another embodiment.
Figure 5B:
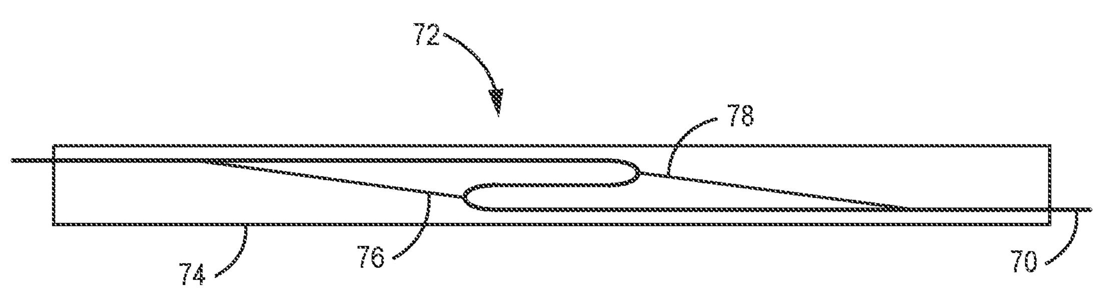
FIG. 5B is a side view of the S-shaped flexible section of FIG. 5A in an extended configuration, according to another embodiment.

A further example of a flexible section 72, according to a further embodiment, is set forth in FIGS. 5A and 5B. In this implementation, the flexible section 72 is a S- or Z-shaped portion 72 of a lead body 70, which is a thin-film lead body 70. The lead body 70 is disposed through a tube 74 that can be sized to fit through a needle as described above. As such, in one implementation, the tube 74 is less than 0.1 inches. In addition, the flexible section 72 of the lead body 60 has flexible restraints 76, 78 attached thereto such that the restraints 76, 78 are attached at one end to the folds or corners of the S-shaped section 72 and at the other end to a portion of the lead body 70 at some length from the flexible section 72 as shown. Thus, in this embodiment, the flexible restraints 76, 78 are the mechanisms by which the flexible section 72 is urged back to its unextended configuration as best shown in FIG. 5A. It is understood that the flexible restraints 76, 78 represent any mechanisms or features that can be coupled to both the S-shaped section 72 and a portion of the lead body 70 at some distance from the S-shaped section 72 and can be used to urge the S-shaped section 72 back to its unextended configuration.

In use, like the S-shaped sections 52, 62 described above, the S-shaped section 72 has an unextended configuration as depicted in FIG. 5A and an extended configuration as shown in FIG. 5B. The description of those configurations and the operation of the S-shaped sections 52, 62 above and the benefits thereof apply equally to this S-shaped section 72. Further, in this embodiment, as mentioned above, the S-shaped section 72 is returned to its unextended configuration with the assistance of the flexible restraints 76, 78.

Figure 6A:
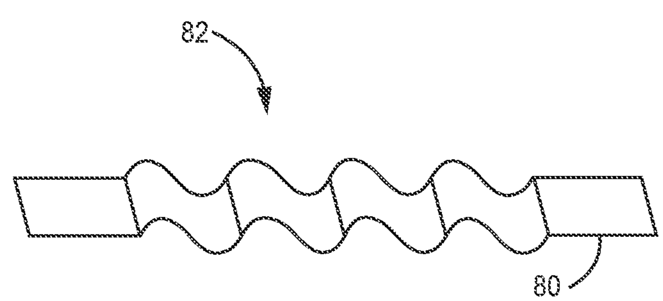
FIG. 6A is a side view of an accordion-like flexible section in a retracted configuration, according to one embodiment.
Figure 6B:
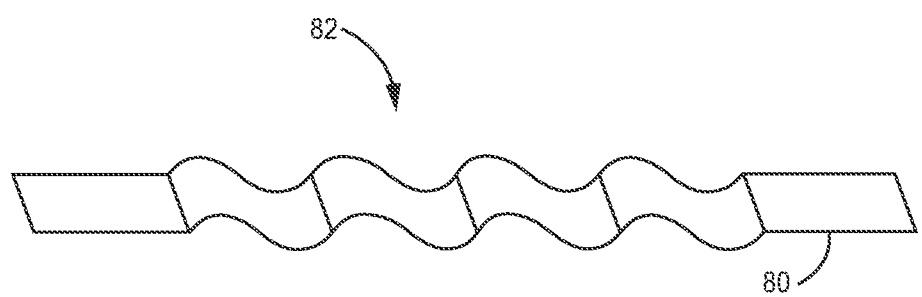
FIG. 6B is a side view of the accordion-like flexible section of FIG. 6A in an extended configuration, according to one embodiment.

Yet another example of a flexible section 82, according to another embodiment, is set forth in FIGS. 6A and 6B. In this implementation, the flexible section 82 is an accordion-like portion 82 of a lead body 80, which is a thin-film lead body 80. In this embodiment, the lead body 80 is not disposed through a tube. The accordion-like portion 82 is a length of the lead body 80 that has a set of partially folded or bent portions that can move between a retracted configuration (as shown in FIG. 6A) and an extended configuration (as shown in FIG. 6B). In this embodiment, the accordion-like portion 82 is configured such that the section 82 is urged toward its retracted configuration when no forces are applied thereto.

In use, and as mentioned above, like the S-shaped sections 52, 62, 72 described above, the S-shaped section 82 has an unextended configuration as depicted in FIG. 6A and an extended configuration as shown in FIG. 6B. The description of those configurations and the operation of the S-shaped sections 52, 62, 72 above and the benefits thereof apply equally to this S-shaped section 82. Further, in this embodiment, as mentioned above, the S-shaped section 82 is returned to its unextended configuration because the accordion-like section 82 is configured such that the section 82 is urged toward that configuration.

Figure 7A:
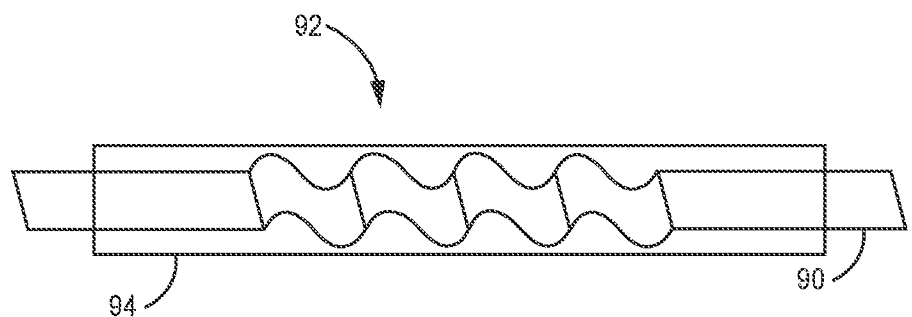
FIG. 7A is a side view of an accordion-like flexible section in a tubular component in a retracted configuration, according to one embodiment.
Figure 7B:
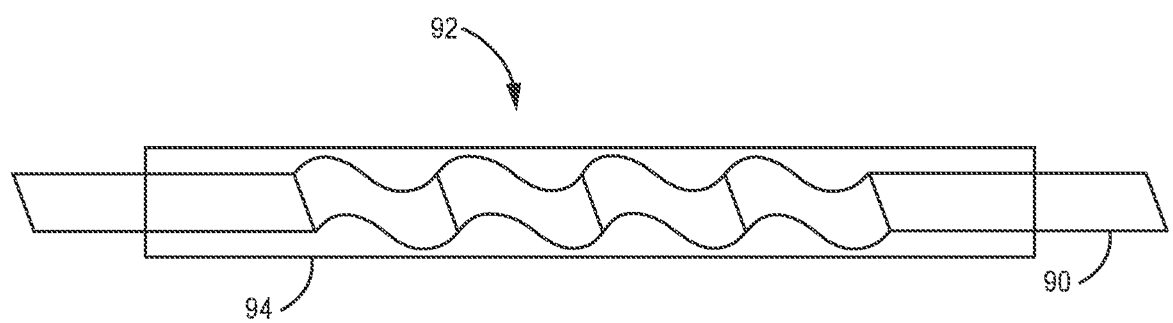
FIG. 7B is a side view of the accordion-like flexible section of FIG. 7A in an extended configuration, according to one embodiment.

Another flexible section 92 embodiment is shown in FIGS. 7A and 7B. In this implementation, the flexible section 92 is an accordion-like portion 92 of a lead body 90, which is a thin-film lead body 90. More specifically, the flexible section 92 is substantially similar to the section 82 discussed above. However, in this embodiment, the lead body 90 is disposed through a tube 94, which can be substantially similar to the tubes in the other embodiments disclosed or contemplated herein. The accordion-like portion 92 is substantially similar to and operates in a substantially similar fashion as the portion 82 in the embodiment above.

Figure 8A:
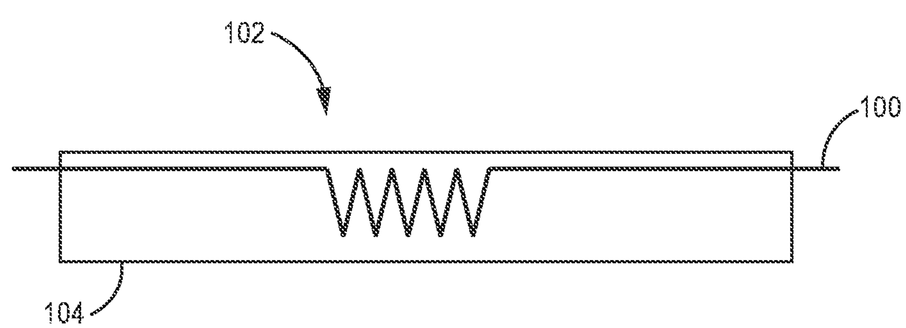
FIG. 8A is a side view of a flexible section having a set of folds or curves in a tubular component in a retracted configuration, according to one embodiment.
Figure 8B:
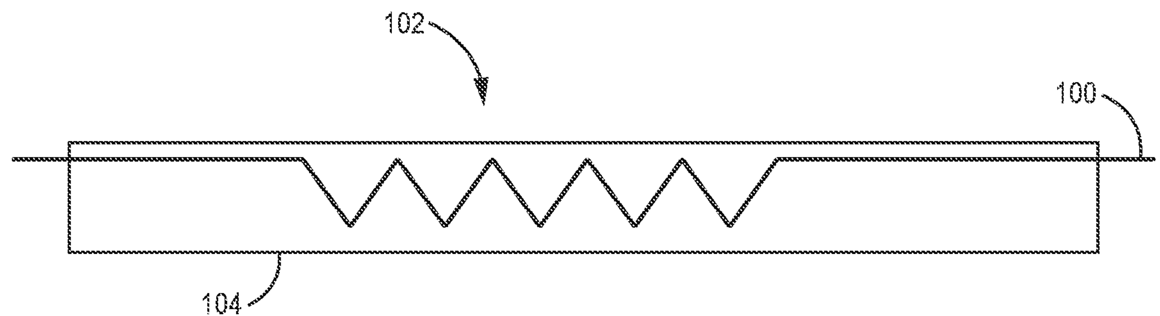
FIG. 8B is a side view of the flexible section of FIG. 8A in an extended configuration, according to one embodiment.

A further example of a flexible section 102, according to another embodiment, is set forth in FIGS. 8A and 8B. In this implementation, the flexible section 102 has a set of folds in the section 102 of a lead body 100, which is a thin-film lead body 100. The lead body 100 is disposed through a tube 104 that can be sized to fit through a needle as described above. As such, in one implementation, the tube 104 is less than 0.1 inches. The flexible portion 102 is a length of the lead body 100 that has a set of folded or bent portions that can move between a retracted configuration (as shown in FIG. 8A) and an extended configuration (as shown in FIG. 8B). In this embodiment, the flexible portion 102 is configured such that the section 102 is urged toward its retracted configuration when no forces are applied thereto.

In use, and as mentioned above, like the flexible sections 52, 62, 72, 82, 92 described above, the flexible section 102 has an unextended configuration as depicted in FIG. 8A and an extended configuration as shown in FIG. 8B. The description of those configurations and the operation of the flexible sections 52, 62, 72, 82, 92 above and the benefits thereof apply equally to this flexible section 102. Further, in this embodiment, as mentioned above, the flexible section 102 is returned to its unextended configuration because the flexible section 102 is configured such that the section 102 is urged toward that configuration.

Figure 9A:
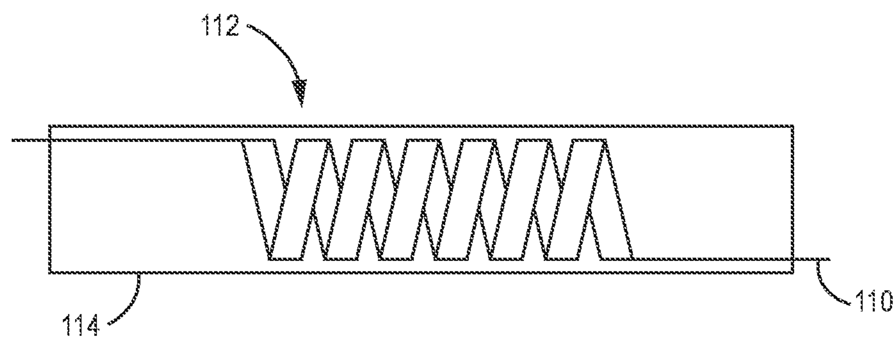
FIG. 9A is a side view of a flexible section having a spiral configuration in a tubular component in a retracted configuration, according to one embodiment.
Figure 9B:
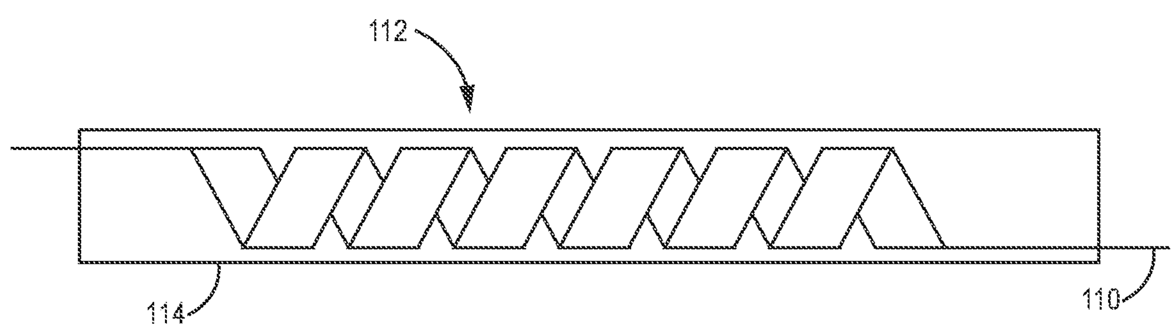
FIG. 9B is a side view of the flexible section of FIG. 9A in an extended configuration, according to one embodiment.

A further example of a flexible section 112, according to another embodiment, is set forth in FIGS. 9A and 9B. In this implementation, the flexible section 112 has a spiral configuration 112 formed in the lead body 110, which is a thin-film lead body 110. The lead body 110 is disposed through a tube 114 that can be sized to fit through a needle as described above. As such, in one implementation, the tube 114 is less than 0.1 inches. The flexible portion 112 is a length of the lead body 110 that has the spiral section 112 that can move between a retracted configuration (as shown in FIG. 9A) and an extended configuration (as shown in FIG. 9B). In this embodiment, the flexible portion 112 is configured such that the section 112 is urged toward its retracted configuration when no forces are applied thereto.

In use, and as mentioned above, like the flexible sections 52, 62, 72, 82, 92, 102 described above, the flexible section 112 has an unextended configuration as depicted in FIG. 9A and an extended configuration as shown in FIG. 9B. The description of those configurations and the operation of the flexible sections 52, 62, 72, 82, 92, 102 above and the benefits thereof apply equally to this flexible section 112. Further, in this embodiment, as mentioned above, the flexible section 112 is returned to its unextended configuration because the spiral section 112 is configured such that the section 112 is urged toward that configuration, perhaps by a shape-memory material or some other known means.

Figure 10A:
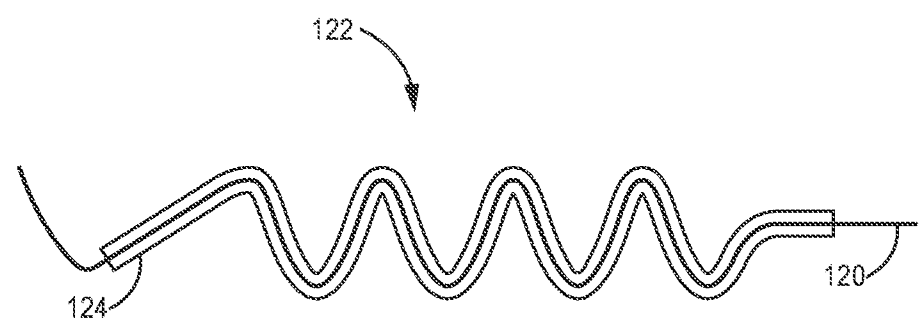
FIG. 10A is a side view of a flexible section having a set of folds or curves in a tubular component in a retracted configuration, according to another embodiment.
Figure 10B:
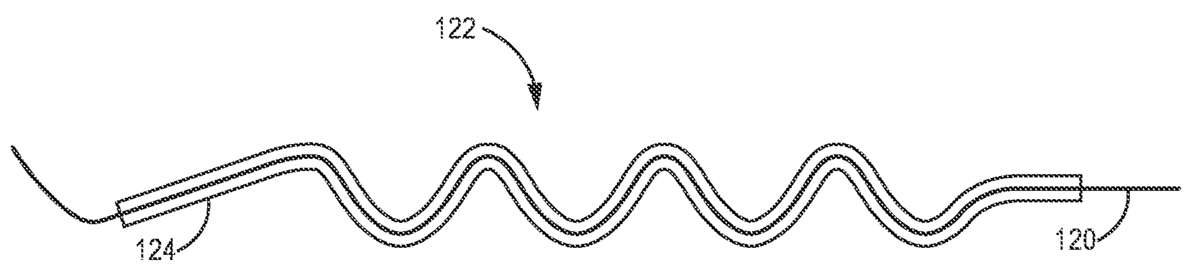
FIG. 10B is a side view of the flexible section of FIG. 10A in an extended configuration, according to another embodiment.

A further example, according to a further embodiment, is a tube 124 with a flexible section 122, as set forth in FIGS. 10A and 10B. In this implementation, the lead body 120 is disposed within a tube 124 having a flexible section 122, wherein the flexible section 122 has series of curves or folds formed in the tube 124 with the thin-film lead body 120 disposed therein. The tube 124 can be sized to fit through a needle as described above. As such, in one implementation, the tube 124 is less than 0.1 inches. The flexible portion 122 is a length of the tube 124 that has the extendable curve section 122 that can move between a retracted configuration (as shown in FIG. 10A) and an extended configuration (as shown in FIG. 10B). In this embodiment, the flexible portion 122 is configured such that the section 122 is urged toward its retracted configuration when no forces are applied thereto.

In use, and as mentioned above, the flexible section 122 has an unextended configuration as depicted in FIG. 10A and an extended configuration as shown in FIG. 10B. The benefits of this flexible section 122 are substantially similar to those described above with respect to other flexible section embodiments. Further, in this embodiment, as mentioned above, the flexible section 122 is returned to its unextended configuration because the flexible section 122 is configured such that the section 122 is urged toward that configuration, perhaps by a shape-memory material or some other known means.

In one embodiment, the tube 124 is formed of silicone or a material containing at least some silicone. Alternatively, the tube 124 can also have silicone potting.

A further example of a flexible section 132, according to a further embodiment, is set forth in FIGS. 11A and 11B. In this implementation, the flexible section 132 is a flexible length 132 of the lead body 130, which is a thin-film lead body 130. The lead body 130 in this implementation is not disposed through a tube. In addition, the flexible section 132 of the lead body 130 has a flexible restraint 134 attached thereto such that the restraint 134 is attached at one end to a first location along the lead body 130 and at the other end to a second location along the lead body 130 at some length from the first location as shown. Thus, in this embodiment, the flexible restraint 134 is the mechanism by which the flexible section 132 is urged back to its unextended configuration as best shown in FIG. 11A. It is understood that the flexible restraint 134 represents any mechanism or feature that can be coupled to the lead body 130 in a similar fashion and can be used to urge the flexible section 132 back to its unextended configuration.

In use, like the flexible section embodiments described above, the flexible section 132 has an unextended configuration as depicted in FIG. 11A and an extended configuration as shown in FIG. 11B. The description of those configurations and the operation of the flexible section embodiments above and the benefits thereof apply equally to this flexible section 132. Further, in this embodiment, as mentioned above, the flexible section 132 is returned to its unextended configuration with the assistance of the flexible restraint 134.

Yet another example of a flexible section 142, according to another embodiment, is set forth in FIGS. 12A and 12B. In this implementation, the flexible section 142, like the flexible section 102 as described above, has a set of folds in the section 142 of a lead body 140, which is a thin-film lead body 140. The flexible section 142 is substantially similar to the section 102 described above, except as explained herein. That is, in this implementation, the flexible section 142 also has an elastic membrane 144 disposed around the flexible section 142 such that the elastic membrane 144 can also stretch or otherwise deform to the same extent as the flexible section 142. In one embodiment, the elastic membrane 144 is formed of silicone or a material that contains silicone. Alternatively, the material can be any known material that can be used in an elastic membrane as described.

In use, like the flexible section embodiments described above, the flexible section 142 has an unextended configuration as depicted in FIG. 12A and an extended configuration as shown in FIG. 12B. The benefits of the various flexible section embodiments described herein apply equally to this flexible section 142. Further, in this embodiment, the flexible section 142 is returned to its unextended configuration because the flexible section 142 is configured such that the section 142 is urged toward that configuration.

In one alternative embodiment as shown in FIG. 12C, the lead body 140 can also have two tabs 146 disposed at each end of the flexible section 142 such that the tabs 146 can help to retain the membrane 144 in position. Further, the tabs 146 can also have anchor openings 148 therein for the same purpose.

Figure 13A:
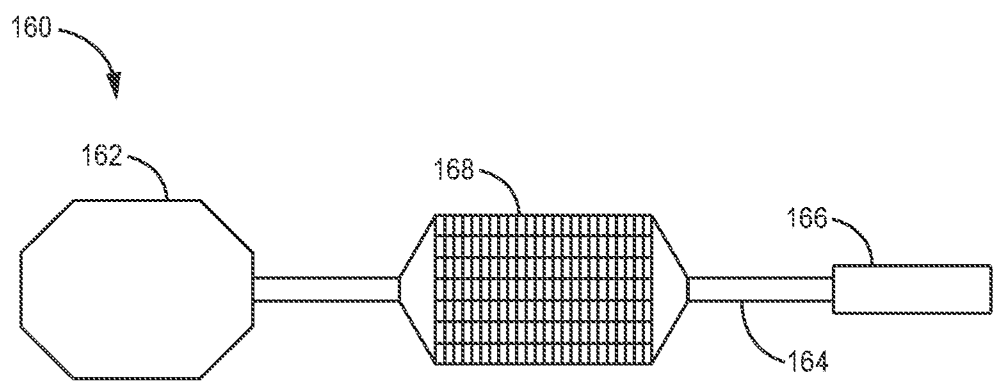
FIG. 13A is a side view of a mesh flexible section in a retracted configuration, according to one embodiment.
Figure 13B:
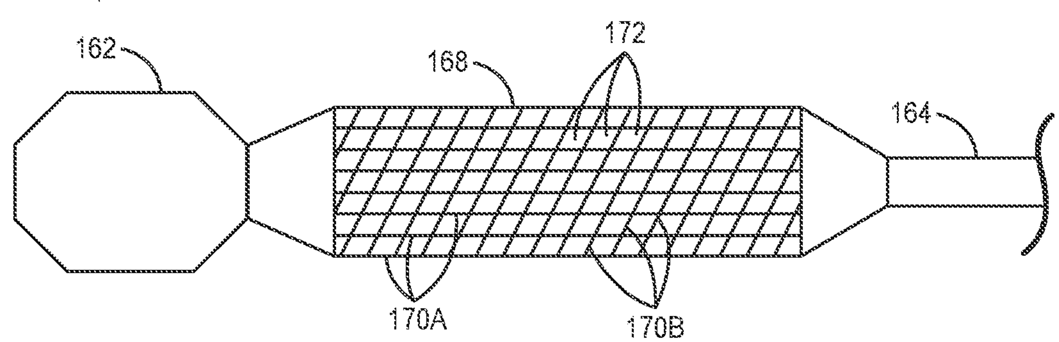
FIG. 13B is a side view of the flexible section of FIG. 13A in an extended configuration, according to one embodiment.

In accordance with a further embodiment, FIGS. 13A and 13B depict another stimulation device 160 for use in stimulation of a patient's spinal cord or peripheral nerves. More specifically, the device 160 is a paddle lead 160 having an electrode body or array (also referred to as a "paddle") 162 on which the one or more electrodes (not shown) are disposed, a lead body (or "tail") 164, a proximal connector 166, and a flexible section 168 along the length of the tail 164. In this implementation, the flexible section 168 is an expandable mesh section 168 of the lead body 164, which is a thin-film lead body 164. The expandable mesh section 168 is a section of the lead body 164 that has a tensioned mesh configuration that can move between a retracted configuration (as shown in FIG. 13A) and an extended configuration (as shown in FIG. 13B). In this embodiment, the mesh section 168 is configured such that the section 168 is urged toward its retracted configuration when no forces are applied thereto. That is, the natural, equilibrium, or resting state of the mesh section 168 is the retracted configuration, such that external force must be applied to the section 168 to urge it into its extended configuration. As such, removal of that external force will result in the mesh section 168 returning to its retracted configuration.

In one embodiment, the mesh section 168 is made up of a material that is tensioned such that the mesh section is in its retracted configuration in its natural state. As best shown in FIG. 13B, the mesh section 168 has elongate lines 170A and transverse lines 170B that are interconnected in such a fashion that there are openings 172 defined therebetween. In the retracted configuration, the elongate lines 170A and transverse lines 170B are retracted into their natural, retracted state such that the lines 170A, 170B are urged into contact with each other, thereby reducing the size of the openings 172 as shown in FIG. 13A. In contrast, in the extended configuration, the elongate lines 170A and transverse lines 170B are urged apart, thereby expanding the size of the openings 172 as shown in FIG. 13B.

The mesh section 168, and more specifically, the lines 170A, 170B can be made of a flexible material. For example, in certain embodiments, the mesh section 168 can be made of peek, polyimides, silicones, epoxy-based materials such as SU-8, polyamides, Pebax, polyeytheylene, other similar materials, or any combination thereof. Alternatively, the mesh section 168 can be made of any known flexible material that has a natural retracted state and an extended, tensioned state such that removal of any external forces causes the flexible material to return to its natural retracted state. Further, the mesh section 168 in certain embodiments has an elastic silicone membrane (not shown) disposed over the material of the section 168. According to some implementations, the membrane can be applied such that the mesh openings 172 are kept open or closed. The membrane can be made of polyurethane, styrene isobutylene styrene, fluoroelestomer, other similar materials, or any combination thereof. Alternatively, the section 168 can have any type of membrane coated over the material of the section 168.

In use, as mentioned above, the mesh section 168 has an unextended configuration as depicted in FIG. 13A and an extended configuration as shown in FIG. 13B. Thus, once the device 160 is implanted into a patient, when any force is applied to either end of the device 160 such that one portion is pulled or urged away from another portion thereof, the mesh section 168 can extend into its extended configuration as shown in FIG. 13B, thereby reducing the chances of the entire device 160 from moving and being displaced as a result of the movement. That is, the expandability and/or flexibility of the mesh section 168 allows both the electrode paddle 162 and the proximal connector 166 to remain in their appropriate positions while any movement is absorbed by the mesh section 168.

Figure 14A:
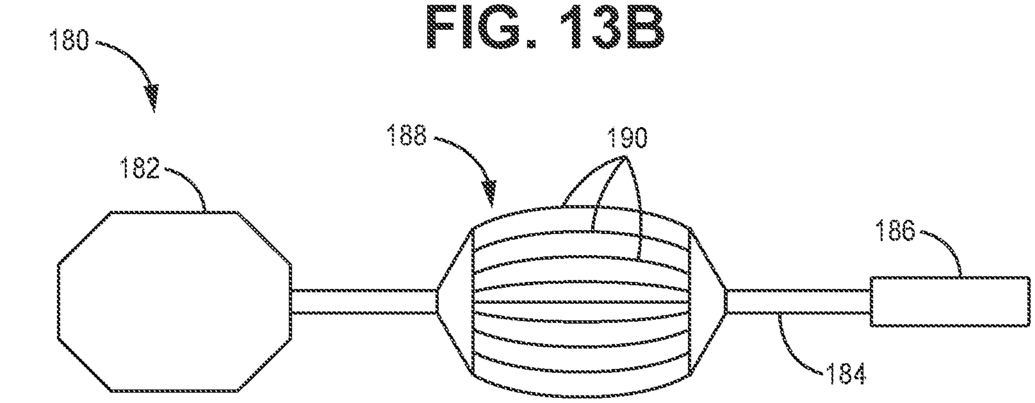
FIG. 14A is a side view of a cord flexible section in a retracted configuration, according to one embodiment.
Figure 14B:
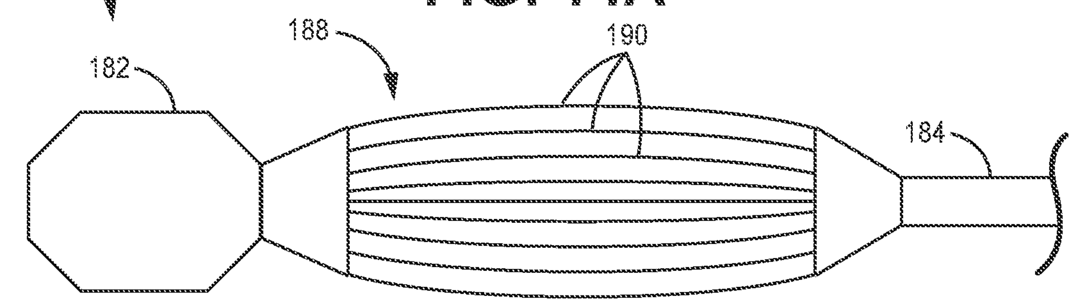
FIG. 14B is a side view of the flexible section of FIG. 14A in an extended configuration, according to one embodiment.

In another implementation, FIGS. 14A and 14B depict another stimulation device 180 for use in stimulation of a patient's spinal cord or peripheral nerves. More specifically, the device 180 is a paddle lead 180 having an electrode body or array (also referred to as a "paddle") 182 on which the one or more electrodes (not shown) are disposed, a lead body (or "tail") 184, a proximal connector 186, and a flexible section 188 along the length of the tail 184. In this implementation, the flexible section 188 is a set of elongate cords 188 attached at each end to the lead body 184, which is a thin-film lead body 184. The expandable cord section 188 is a section of the lead body 164 that has multiple tensioned cords 190 that can move between a retracted configuration (as shown in FIG. 14A) and an extended configuration (as shown in FIG. 14B). In this embodiment, the cord section 188 is configured such that the section 188 is urged toward its retracted configuration when no forces are applied thereto. That is, the natural, equilibrium, or resting state of each of the cords 190 is the retracted configuration, such that external force must be applied to the section 188 to urge it into its extended configuration. As such, removal of that external force will result in the cord section 188 returning to its retracted configuration.

In one embodiment, each of the cords 190 is made up of an elastic material that is tensioned such that the cord section 188 is in its retracted configuration in its natural state. That is, as mentioned above, in the retracted configuration, the cords 190 are retracted into their natural, retracted state. In contrast, in the extended configuration, the cords 190 are urged into their elongated or stretched configurations, thereby resulting in the extended configuration as shown in FIG. 14B.

While the term "cords" is used herein to describe the elongate components 190, it is understood that the elongate components 190 can be cables, ropes, strings, threads, or any other known types of elongate components made of an elastic material. In certain embodiments, the cords 190 can be made of peek, polyimides, silicones, epoxy-based materials, polyurethane, styrene isobutylene styrene, fluoroelastomer, other biocompatible polymers, or any combination thereof. In other embodiments, a shape memory material such as nitinol or an elgiloy spring can be used in conjunction with one or more elastomeric or non-elastomeric materials. Alternatively, the cords 190 can be made of any known elastic material that has a natural retracted state and an extended, tensioned state such that removal of any external forces causes the elastic material to return to its natural retracted state.

In certain implementations, the cords 190 can have an elastic silicone membrane coating disposed over the material of the cords 190. Alternatively, the cords 190 can have any type of membrane coated thereover.

In use, as mentioned above, the cord section 188 has an unextended configuration as depicted in FIG. 14A and an extended configuration as shown in FIG. 14B. Thus, once the device 180 is implanted into a patient, when any force is applied to either end of the device 180 such that one portion is pulled or urged away from another portion thereof, the cord section 188 can extend into its extended configuration as shown in FIG. 14B, thereby reducing the chances of the entire device 180 moving and being displaced as a result of the movement. That is, the expandability and/or flexibility of the cord section 188 allows both the electrode paddle 182 and the proximal connector 186 to remain in their appropriate positions while any movement is absorbed by the cord section 188.

In a further alternative, the devices 180 shown in FIGS. 14A and 14B can be two different versions of a similar device in which the cord sections 188 are flexible, but not elastic. That is, while the cords 190 have some capability to stretch a minimal amount, it is a small percentage of their original length. As such, the device 180 in FIG. 14A has a flexible section 188 that has a first, shorter length in comparison to the second, longer flexible section 188 of the device 180 in FIG. 14B. In one embodiment, the individual cables 190 are coated in an elastic silicone membrane. Alternatively, in another implementation, the separate cords 190 in these non-stretchy embodiments can have an inner core of or be embedded in a supporting elastic material such as silicone to maintain the shape of the cords 190 by keeping the cords 190 under slight tension in the resting position and allowing deformation thereof if sufficient force is applied.

Further implementations of the various device embodiments disclosed or contemplated herein can also include a flexible electrode array. That is, any stimulation device as contemplated herein for use in stimulation of a patient's spinal cord or peripheral nerves can have a flexible electrode array or an electrode array with a flexible section. Such a flexible electrode array can be the sole flexible section in the device, or it can be combined in the device with a flexible section in the lead body according to any such embodiments herein.

Figure 15:
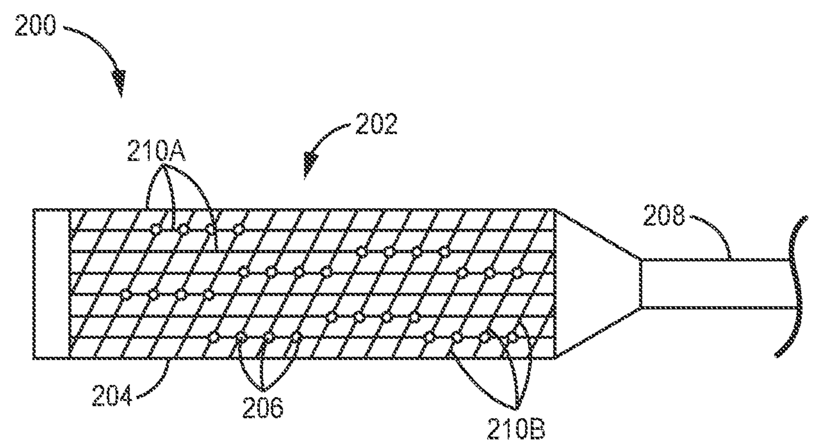
FIG. 15 is a side view of a mesh flexible section in an electrode body, according to one embodiment.

FIG. 15, according to one embodiment, depicts the electrode body or array 202 of a stimulation device 200 in which the electrode paddle 202 has a flexible section 204. More specifically, the device 200 is a paddle lead 200 in which the paddle 202 has a flexible section 204 with a plurality of electrode contacts 206 disposed thereon. The paddle 202 is coupled to a lead body (or "tail") 208. FIG. 15 is an expanded view of the paddle 202 such that the remainder of the components, including, for example, the proximal connector, are not shown. In this implementation, the flexible section 204 is an expandable mesh section 204 of the paddle 202. The expandable mesh section 204 is a section of the paddle 202 that has a tensioned mesh configuration that can move between a retracted configuration in a fashion similar to the mesh section 168 described above with respect to FIGS. 13A and 13B. All of the components, features, and characteristics of this section 204 are substantially similar to that section 168 except as discussed herein. In addition, the mesh section 204 in this embodiment has a plurality of electrode contacts 206 disposed thereon as shown. In FIG. 15, the contacts 206 are disposed various intersections of the elongate lines 210A and the transverse lines 210B. Alternatively, the contacts 206 can be disposed anywhere on the mesh section 204.

In use, as mentioned above, the mesh section 204 has an unextended configuration and an extended configuration. Thus, once the device 200 is implanted into a patient, when any force is applied to electrode paddle 202, the mesh section 204 can extend toward and/or into its extended configuration, thereby reducing the chances of the entire paddle 202 from moving and being displaced as a result of the movement. Further, the flexible section 204 allows the paddle 202 to deform and conform more easily to the shape of the surface on which the paddle 202 is disposed. Thus, the expandability and/or flexibility of the mesh section 204 allows the electrode paddle 202 to remain in its appropriate position while any movement is absorbed by the mesh section 204.

Figure 16:
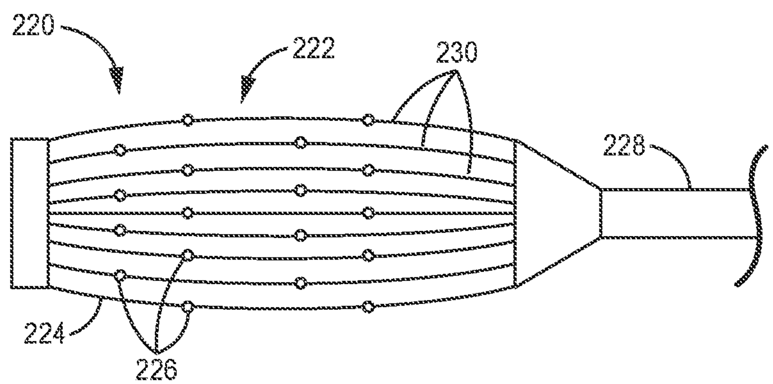
FIG. 16 is a side view of a cord flexible section in an electrode body, according to one embodiment.

In another implementation, FIG. 16 depicts another stimulation device 220 that is a paddle lead 220 having an electrode body or array (also referred to as a "paddle") 222 with a flexible section 224 on which the one or more electrodes 226 are disposed and a lead body (or "tail") 228 connected thereto. More specifically, FIG. 16 is an expanded view of the paddle 222 such that the remainder of the components, including, for example, the proximal connector, are not shown. In this implementation, the flexible section 224 is a set of elongate cords 230 attached at each end to the paddle 222. The expandable cord section 224 is a section of the paddle 222 that has multiple tensioned cords 230 that can move between a retracted configuration and an extended configuration in a fashion similar to the cord section 188 described above with respect to FIGS. 14A and 14B. All of the components, features, and characteristics of this section 224 are substantially similar to that section 188 except as discussed herein. In addition, the cord section 224 in this embodiment has a plurality of electrode contacts 226 disposed on the cords 230 as shown. It is understood that the contacts 226 can be disposed anywhere on the cord section 224.

In use, as mentioned above, the cord section 224 has an unextended configuration and an extended configuration. Thus, once the device 220 is implanted into a patient, when any force is applied to the electrode paddle 222, the cord section 224 can extend into its extended configuration, thereby reducing the chances of the entire paddle 222 moving and being displaced as a result of the movement. Further, the flexible section 224 allows the paddle 222 to deform and conform more easily to the shape of the surface on which the paddle 222 is disposed. Thus, the expandability and/or flexibility of the cord section 224 allows both the electrode paddle 222 to remain in its appropriate position while any movement is absorbed by the cord section 224.

While many of the flexible sections in the various embodiments herein are described solely as flexible, it is understood that any of these sections can also be elastic. As such, any of the flexible sections can be capable of being easily stretched or expanded and subsequently resuming its former shape upon removal of the stretching or expanding force.

Figure 17:
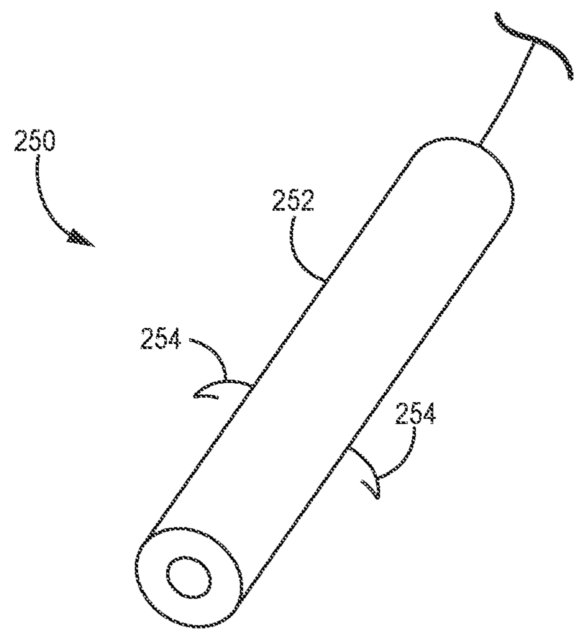
FIG. 17 is a perspective view of a percutaneous lead device with attachment barbs, according to one embodiment.

Any of the stimulation devices disclosed or contemplated herein can also have attachment barbs or similar components disclosed on the electrode body thereof. For example, FIGS. 17 and 18 each depict a stimulation device 250, 260 for use in stimulation of a patient's spinal cord or peripheral nerves. More specifically, the lead 250 in FIG. 17 is a percutaneous lead 250 having an electrode body 252 on which one or more attachment components 254 are disposed. In this embodiment, there are two attachment components 254 that are two barbs 254 attached to the body 252. The attachment components 254 are configured to assist with attaching the electrode body 252 to the target tissue in the patient. Alternatively, any known attachment component in any number ranging from one to any number of attachment components that could be useful can be incorporated into any of the device embodiments disclosed or contemplated herein.

Figure 18:
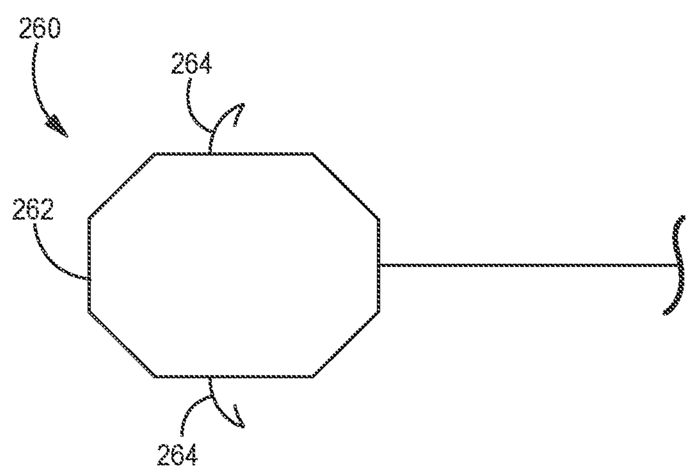
FIG. 18 is a side view of a paddle lead device with attachment barbs, according to one embodiment.

Similarly, the lead 260 in FIG. 18 is a paddle lead 260 having an electrode body 262 on which one or more attachment components 164 are disposed. In this embodiment, there are two attachment components 264 that are two barbs 264 attached to the body 262. The attachment components 264 are configured to assist with attaching the electrode body 262 to the target tissue in the patient. Alternatively, any known attachment component in any number ranging from one to any number of attachment components that could be useful can be incorporated into any of the device embodiments disclosed or contemplated herein.

Figures 19A, 19B, 20A, 20B:
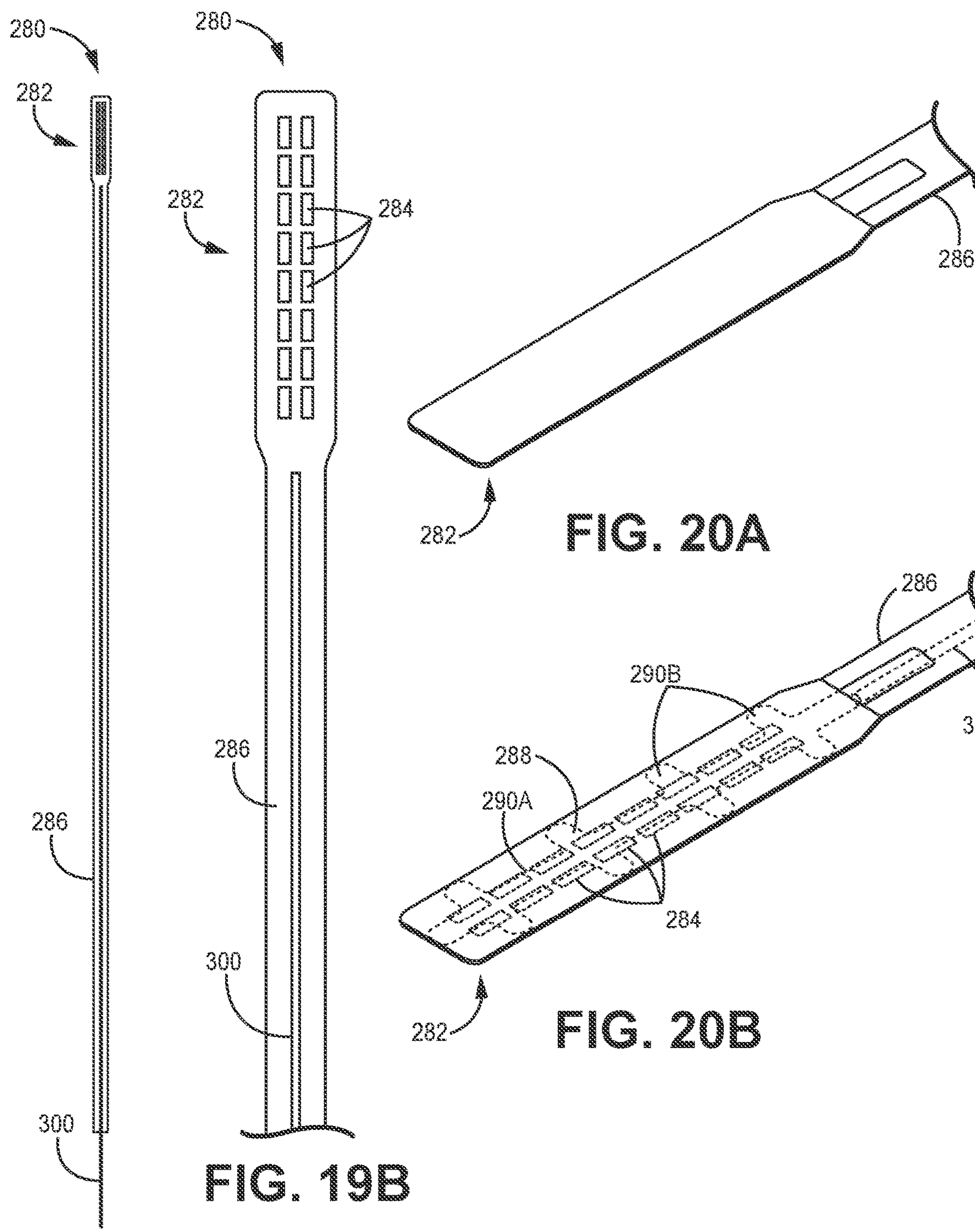
FIG. 19A is a side view of a percutaneous paddle lead device with a deployable paddle, according to one embodiment.
FIG. 19B is an expanded side view of the paddle of the paddle lead device of FIG. 19A, according to one embodiment.
FIG. 20A is an expanded perspective view of the paddle of the paddle lead device of FIG. 19A, according to one embodiment.
FIG. 20B is another expanded perspective view of the paddle of the paddle lead device of FIG. 19A, according to one embodiment.

Another embodiment of a percutaneously deliverable stimulation device 280 for use in stimulation of a patient's spinal cord or peripheral nerves is shown in FIGS. 19A-20B. As best shown in FIGS. 19A and 19B, the lead 280 has a deployable electrode paddle (also referred to as a "grid" or "array") 282 on which a plurality of electrodes 284 are disposed, a lead body (also referred to as a "tail") 286 coupled to the paddle 282, and a connection component (also referred to as a "connector") (not shown) at a proximal end of the lead body 286 to which the external electrical source is coupled. In addition, the lead body 286 is configured to receive a delivery device (such as device XXX as discussed in additional detail below and depicted in FIGS. 19A, 21A, and 21C) such that the device can be disposed through or alongside the lead body 286 to provide structural support to the body 286 as the device 280 is percutaneously introduced via a needle or other shaft to the desired target area in the patient.

In various implementations herein, both the electrode paddle 282 and the lead body 286 are both thin film components. As such, both the electrode paddle 282 and the lead body 286, along with the other components in the instant device 280 equivalent to those components described in the other embodiments discussed above, can be made of the same materials and can have any of the same characteristics and features as those other embodiments as described in detail above, except as discussed herein.

The electrode paddle 282 is depicted in additional detail according to one embodiment in FIGS. 20A and 20B. The paddle 282 has a plurality of electrode contacts 284 as shown. In certain implementations, the paddle 282 has an even number of evenly spaced contacts 284. For example, according to one specific exemplary embodiment, the paddle 282 has 16 electrode contacts 284. Alternatively, the paddle can have 32 electrode contacts 284. In a further alternative, the paddle 282 can have any number of contacts 284.

The paddle 282 is configured to move between a retracted or delivery configuration and an expanded or deployed configuration, which is the flat configuration as shown in FIGS. 20A and 20B. Deployment from the undeployed configuration to the deployed configuration is accomplished via a deployment mechanism (also referred to as a "spine") 288 that is attached to the paddle 282 as shown in FIG. 20B. The deployment mechanism 288 is made of a shape memory material such as nitinol (or any other shape member material disclosed herein or any other known shape memory material) that is configured to be in its resting or natural state in the flat configuration. Thus, when the paddle 282 is urged into a smaller configuration (such as a cylindrical shape, for example), the deployment mechanism 288 will be tensioned such that when the external force(s) being applied to the paddle 282 are released, the deployment mechanism 288 will urge the paddle 282 back into the flat (deployed) configuration. In one embodiment, the deployment mechanism 288 is attached to an external surface of the paddle 282 on an opposite side of the paddle 282 from the side on which the electrode contacts 284 are disposed. Alternatively, the mechanism 288 can be embedded within the paddle 282. The deployment mechanism 288 as shown has an elongate body 290A with multiple wings 290B extending therefrom. Alternatively, the deployment mechanism 282 can have any shape or configuration that allows for deploying the paddle 282 into the flat (deployed) configuration.

Figure 21A:
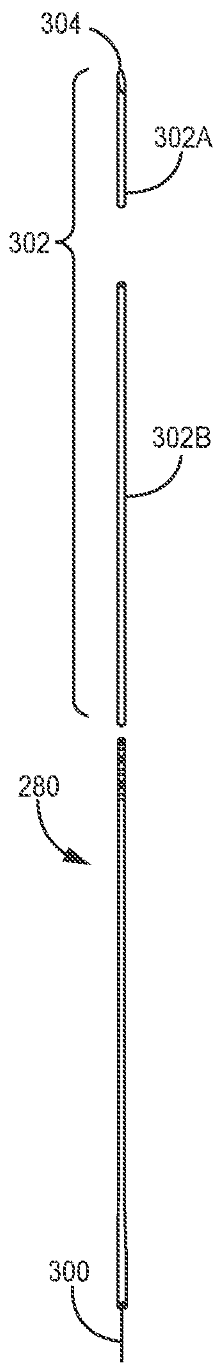
FIG. 21A is an exploded side view of the percutaneous paddle lead device of FIG. 19A with delivery device and a delivery shaft, according to one embodiment.

The delivery components used for delivering the device 280 to the target area will now be discussed. As best shown in FIG. 21A, the device 280 is delivered to the target area via a delivery device 300 that is coupled or otherwise associated with the lead device 280 such that the delivery device 300 can be used to urge the lead device 280 into the desired position. In this specific exemplary embodiment, the delivery device 300 is a substantially stiff wire or rod such as or similar to a push rod, stylet, or guidewire.

Further, the lead device 280 is delivered via an elongate delivery shaft (also referred to as a "needle") 302 such that the lead device 280 is positioned in the delivery shaft 302 such that the shaft 302 can be positioned as desired before the lead device 280 is urged out of the shaft 302 via the delivery device 300. It is understood that certain embodiments of this shaft 302 can have the same dimensions, characteristics, and features as the needle embodiments discussed above. The delivery shaft 302 has a sharp tip 304 at its distal end such that the tip 304 can be used to pierce the patient's skin and tissue and the delivery shaft 302 be inserted through and into the desired position in the patient. In the implementation as shown, the delivery shaft 302 is actually made up of two components: a distal shaft 302A and a proximal shaft 302B. The proximal shaft 302B is positionable within the distal shaft 302A. Alternatively, the delivery shaft 302 can be a single unitary component.

The stimulation device 280 can be positioned within (and inserted through) the delivery shaft 302. More specifically, the paddle 282 can be folded or otherwise urged into a smaller cross-section (such as, for example, a cylindrical shape) such that the paddle 282 can fit within and through the shaft 302. For example, in FIG. 21B, the paddle 282 is disposed in a cylindrical shape and positioned within the shaft 302.

Figure 21B:
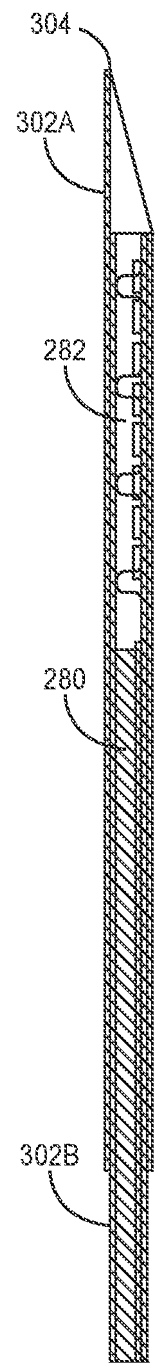
FIG. 21B is an exploded cross-sectional view of the percutaneous paddle lead device of FIG. 19A disposed within the delivery shaft of FIG. 21A, according to one embodiment.
Figure 21C:
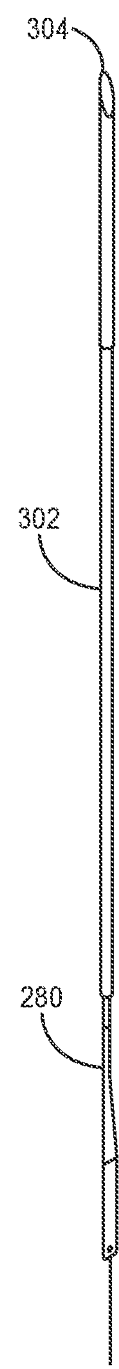
FIG. 21C is a side view of the percutaneous paddle lead device of FIG. 19A disposed within the delivery shaft of FIG. 21A, according to one embodiment.

In use, the stimulation device 280 as shown in FIG. 21A is inserted into the delivery shaft 302 via the delivery device 300 such that the device 280, including the paddle 282, are disposed within the shaft as shown in FIGS. 21B and 21C. At this point, the delivery shaft 302 is urged through the patient's skin and tissue via the sharp tip 304 until the distal end of the shaft 302 is disposed at the desired location. Once the shaft 302 is positioned as desired, the shaft 302 is removed while retaining the stimulation device 280 in place via the delivery device 300. The removal of the shaft 302 causes the paddle 282 to deploy via the action of the deployment mechanism 288 as described above. Once the shaft 302 has been removed and the paddle 282 is deployed, the delivery device 300 can also be removed, leaving the stimulation device 280 positioned as needed within the patient.

The use of a deployable flat paddle 282 with a plurality of electrode contacts 284 thereon provides maximum coverage at the treatment site while also making it possible to reduce the cross-sectional profile by deforming or bending the paddle 282 to fit through a delivery shaft 302 for delivering the stimulation device 280. The wider electrode contact area of the paddle 282 in comparison to known percutaneous lead options will provide more coverage and better procedural success while being less invasive than the known paddle/grid electrode array options.

It is understood that the device 280 described above can also have any of the features of any of the other embodiments herein incorporated therein, including any flexible section implementation as described herein in the elongate lead body 286 and/or the paddle 282.

According to another implementation, any of the device embodiments disclosed or contemplated herein can also include a drug delivery component or mechanism. For example, any of the device embodiments can include a lumen defined with the lead body and/or the electrode body such that a treatment fluid can be delivered via that lumen to the target tissue via the device. Alternatively, any other known treatment agent delivery mechanism or feature can be incorporated into any of the embodiments herein, including, for example, a time-release mechanism, a treatment agent coating, an actuable agent delivery mechanism (actuated by some external stimulation), a treatment agent capsule, or any other such mechanism, method, or feature.

Although various exemplary implementations have been described herein, persons skilled in the art will recognize that changes may be made in form and detail without departing from the spirit and scope thereof.

What is claimed is:

1. A spinal cord stimulation device comprising:

(a) an elongate thin film lead body comprising a flexible section disposed along a portion of the elongate thin film lead body, wherein the flexible section comprises an expandable mesh, the expandable mesh configured to move between:

(i) a retracted configuration in which a proximal end and a distal end of the lead body are disposed at a first distance from each other; and (ii) an extended configuration in which the proximal end and the distal end of the lead body are disposed at a second distance from each other, wherein the second distance is greater than the first distance; and (b) a thin film electrode body coupled to the distal end of the elongate thin film lead body.

2. The spinal cord stimulation device of claim 1, further comprising at least two attachment barbs disposed on the thin film electrode body.

3. The spinal cord stimulation device of claim 1, wherein the flexible section has a first end coupled to a distal portion of the elongate thin film lead body and a second end coupled to a proximal portion of the elongate thin film lead body.

4. The spinal cord stimulation device of claim 1, wherein the stimulation device is a percutaneous lead device or a paddle lead device.

5. The spinal cord stimulation device of claim 1, wherein the expandable mesh comprises a plurality of openings defined therein, wherein the spinal cord stimulation device further comprises a proximal connector coupled to the proximal end of the lead body, and wherein movement of the expandable mesh between the retracted position and the extended position is configured to absorb movement of the spinal cord stimulation device while maintaining appropriate positioning of the thin film electrode body and the proximal connector.

6. The spinal cord stimulation device of claim 1, further comprising an elastic membrane disposed around the flexible section.

7. The spinal cord stimulation device of claim 1, further comprising a second flexible section disposed within the electrode body.

8. A spinal cord stimulation device comprising:

(a) an elongate lead body positionable through an elongate tube, the elongate lead body having a proximal end and a distal end;

(b) an electrode body disposed at the distal end of the elongate lead body; and (c) a flexible section disposed along a length of the elongate lead body and moveable between a retracted configuration and an extended configuration, the elongate lead body having a shorter length when the flexible section is in the retracted configuration than when the flexible section is in the extended configuration, wherein the flexible section comprises an expandable mesh comprising a plurality of openings defined therein, wherein the elongate lead body is a thin film component.

9. A spinal cord stimulation device comprising:

(a) an elongate lead body having a proximal end and a distal end;

(b) a substantially flat electrode body disposed at the distal end of the elongate lead body; and (c) a first flexible section disposed within the substantially flat electrode body, the first flexible section comprising an expandable mesh configured to move between:

(i) an axially retracted configuration; and (ii) an axially extended configuration; and (d) a second flexible section disposed along a length of the elongate lead body, wherein the elongate lead body and the substantially flat electrode body are thin film components, and wherein the second flexible section is configured to absorb movement of the spinal cord stimulation device to maintain positioning of the substantially flat electrode body.

10. The spinal cord stimulation device of claim 9, further comprising at least two attachment barbs disposed on the substantially flat electrode body.

11. The spinal cord stimulation device of claim 9, wherein the stimulation device is a percutaneous lead device or a paddle lead device.

12. The spinal cord stimulation device of claim 9, wherein one or more of the first flexible section and the second flexible section comprises a plurality of openings defined therein.

13. A spinal cord stimulation device comprising:

(a) an elongate lead body having a proximal end and a distal end;

(b) a deployable electrode array disposed at the distal end of the elongate lead body, the deployable electrode array comprising:

(i) a deployable electrode array body;

(ii) a plurality of electrode contacts disposed on the deployable electrode array body;

(iii) a delivery configuration in which the deployable electrode array body has a reduced profile;

(iv) a deployed configuration in which the deployable electrode array body has an expanded, flat profile; and (v) a deployment spine associated with and extending along a length of the deployable electrode array body, the deployment spine comprising a shape memory material and having at least one wing extending outwardly from each side of the deployment spine, wherein the deployment spine is configured to urge the deployable electrode array body into the deployed configuration, wherein the elongate lead body and the deployable electrode array are thin film components.

14. The spinal cord stimulation device of claim 13, wherein the device is positionable within a delivery shaft.

15. The spinal cord stimulation device of claim 13, wherein the delivery configuration is a substantially cylindrical configuration.

16. The spinal cord stimulation device of claim 13, wherein the shape memory material of the deployment spine is embedded within the deployable electrode array body, and wherein the shape memory material is configured to urge the deployable electrode array into the expanded, flat profile when the deployable electrode array is in the deployed configuration.

17. The spinal cord stimulation device of claim 13, wherein the shape memory material of the deployment spine is attached to the deployable electrode array body, and wherein the shape memory material is configured to urge the deployable electrode array into the expanded, flat profile when the deployable electrode array is in the deployed configuration.

* * * * *